United States Patent [19]

Hurlock

[11] 3,989,754

[45] Nov. 2, 1976

[54] METHOD OF IMPROVING THE REMOVAL OF MOTHER LIQUOR FROM ACRYLAMIDE CRYSTALS

[75] Inventor: John R. Hurlock, Hickory Hills, Ill.

[73] Assignee: Nalco Chemical Company, Oak Brook, Ill.

[22] Filed: Nov. 19, 1975

[21] Appl. No.: 633,358

[52] U.S. Cl. .............................................. 260/561 N
[51] Int. Cl.² ..................................... C07C 103/133
[58] Field of Search ................................. 260/561 N

[56] References Cited
UNITED STATES PATENTS

| | | | |
|---|---|---|---|
| 2,690,454 | 9/1954 | Strain et al. | 260/561 N |
| 3,301,900 | 1/1967 | Talet | 260/561 N |
| 3,624,153 | 11/1971 | Lynch et al. | 260/561 N |

OTHER PUBLICATIONS

Yamashita et al., Chem. Abstracts, 82, (1975), No. 73632.

*Primary Examiner*—Arthur P. Demers
*Attorney, Agent, or Firm*—John G. Premo; Robert A. Miller; Barry W. Sufrin

[57] ABSTRACT

Mother liquor removal from acrylamide crystals is improved by draining such crystals in the presence of a paraffinic hydrocarbon liquid.

3 Claims, 1 Drawing Figure

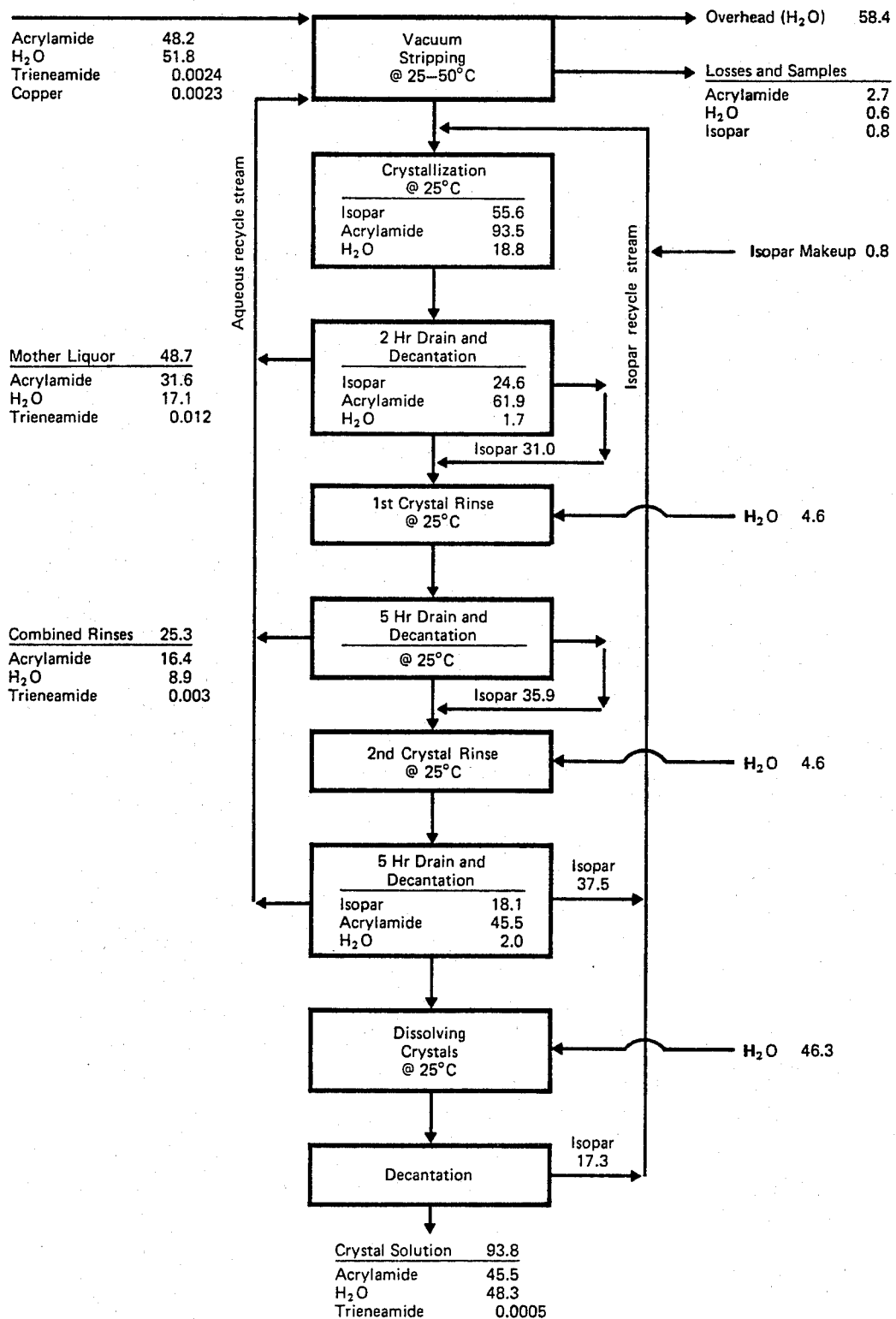

METHOD OF IMPROVING THE REMOVAL OF MOTHER LIQUOR FROM ACRYLAMIDE CRYSTALS

Commercially, most acrylamide monomer is produced by the hydration of acrylonitrile with water in the presence of a catalyst. The catalysts used in these processes may be selected from a variety of metals with the most common metallic catalyst being some form of copper. For further details with respect to the hydration of acrylonitrile with water in the presence of metallic catalysts, reference may be made to the following U.S. Pat. Nos.

| | |
|---|---|
| U.S. Pat. No. 3,597,481; | U.S. Pat. No. 3,642,643; |
| U.S. Pat. No. 3,631,104; | Canadian Pat. No. 839,384 (1972). |
| U.S. Pat. No. 3,642,894; | |

Most of the processes described in the above patents produce aqueous solutions of acrylamide. When it is desired to produce crystalline or dry acrylamide from these solutions, it is customary to remove the water therefrom by evaporative techniques. A commonly practiced water removal system utilizes vacuum stripping of the water from the acrylamide solution at 20 millimeters using temperatures ranging between 20° – 60° C. After approximately an 80% solution of acrylamide is produced under these conditions, the temperature of the now super-saturated acrylamide solution is reduced, which causes most of the acrylamide contained in the supersaturated solution to precipitate in the form of white, needle-like crystals. After gross mechanical separation of the excess water, there remains a filter cake of acrylamide which contains relatively large quantities of mother liquor. Conventional filtration techniques short of high-speed centrifuging are incapable of removing this mother liquor from the crystals even though the crystals are allowed to drain for periods as long as 24 hours.

The mother liquor containing crystals produced as described above in addition to being difficult to drain are oftentimes contaminated with an undesirable, unsaturated chemical reactant which I prefer to call trienamide. This material is detectable by means of either gas chromotography or mass spectometry but its exact structure is unknown. It is believed to be a diene or trienamide which results from contamination of the acrylonitrile from which the acrylamide is synthesized.

It is now known that this trienamide can be successfully removed from acrylamide crystals by one or more water washings. While water washing removes the trienamide impurities, it also dissolves acrylamide; therefore, if large quantities of water are used to wash the crystals, substantial product is dissolved which must be recovered by means of process recycle or additional processing steps.

If it were possible to increase the drainage time of acrylamide crystalline cakes which contain substantial quantities of mother liquor or wash water without necessitating the use of centrifuges and other expensive equipment, a valuable contribution to the art would be made. Also, if it were possible to provide a means for effectively washing acrylamide crystals to remove trienamide therefrom using only small quantities of water, such would be an advantage in the commercial processing of these crystals.

THE INVENTION

In accordance with the invention, it has been found that an improved method for removing mother liquor from acrylamide crystals is afforded which comprises precipitating the acrylamide crystals from their mother liquor in the presence of a water-insoluble paraffinic hydrocarbon liquid. After the crystals are precipitated, the mother liquor, which is entrained within such crystals as well as the water insoluble paraffinic hydrocarbon liquid, is drained therefrom and the thus drained crystals are recovered. In a more specific embodiment of the invention, the crystals treated in accordance with the above may be slurried in additional paraffinic hydrocarbon liquid, washed with small amounts of water to remove impurities from the crystals, drained, and then either collected for use or re-washed to produce relatively pure crystalline acrylamide.

As indicated earlier, the chief advantage of the invention resides in the fact that by utilizing the water insoluble paraffinic hydrocarbon liquid, it is possible to remove from a mother liquor wet cake of crystalline acrylamide over 90% of the mother liquor which is entrained therein. Without this treatment, if the wet cake were allowed to merely gravity drain without additional treatment, approximately 50% of the mother liquor would gravity separate.

The Water-Insoluble Paraffinic Hydrocarbon Liquid

The water insoluble paraffinic hydrocarbon liquid may be selected from a relatively large group of hydrocarbon liquids. In a preferred embodiment, the hydrocarbon liquids are of the type derived from the refining of petroleum and are, therefore, oftentimes mixtures. In a most preferred embodiment of the invention, the paraffin hydrocarbon liquid is predominantly branch chained in structure and has a molecular weight of 100 – 300. It may contain as much as 20% cycloaliphatic hydrocarbon compounds. A preferred material that is commercially available is sold under the trade name, ISOPAR M, and has the following properties and characteristics:

TABLE 1

| Specification properties | Minimum | Maximum | Test method |
|---|---|---|---|
| Gravity, API at 60/60° F | 48.0 | 51.0 | ASTM D 287 |
| Color, Saybolt | 30 | | ASTM D 156 |
| Aniline point, ° F | 185 | | ASTM D 611 |
| Sulfur, p.p.m. | | 10 | ASTM D 1266[1] |
| Distllation, ° F | | | ASTM D 86 |
| IBP | 400 | 410 | |
| Dry point | | 495 | |
| Flash point, ° F (Pennsky-Martens closed cup). | 160 | | ASTM D 93 |
| Composition | | | Test Method |
| Average molecular weight | 177 | | Calculated |
| Hydrocarbon type, vol % | | | Mass spectrometer |

TABLE 1-continued

| | |
|---|---|
| Isoparaffins | 80.0 |
| Normal paraffins | <0.5 |
| Total paraffins | 80.0 |
| Naphthenes: | |
| 1-ring | 16.2 |
| 2-ring | 3.2 |
| 3-ring | 0.3 |
| 4-ring | 0.0 |
| Total Naphthenes | 19.7 |
| Mono aromatics | 0.3 |

[1]Nephelometric mod.

While ISOPAR M represents a preferred paraffinic hydrocarbon liquid, it is understood that other petroleum fractions or blends such as naphthas, Skellysolves, and other similar petroleum fractions may be used. Similarly, pure hydrocarbons such as decane, dodecane and the various branch chained isomers of such compounds may be used.

It will be understood that the paraffinic hydrocarbon liquid may contain small amounts, e.g. up to 5% by weight, of aromatic liquids, hydrocarbons such as, for instance, benzene, toluene, xylene, and the like.

The amount of the water insoluble paraffinic hydrocarbon liquid that is used to treat the acrylamide crystalline cake which contains either mother liquor or wash water should be that amount sufficient to enable the crystals to be formed into a workable, relatively non-viscous slurry. As a general rule, amounts of the paraffinic hydrocarbon liquid used in relation to the dry crystals present in the cake varies between about 20% by weight to about 50% by weight. It should be understood that the particular amount required can be readily determined by routine experimentation.

General Technique for Practicing Invention

In order to maximize the efficiency of operations when the process of the invention is practiced, it is beneficial that the paraffinic hydrocarbon liquid be added to the acrylamide water solution prior to its being precipitated. This means that in most instances the paraffinic hydrocarbon will be added to the saturated acrylamide solution while it is still hot, e.g. 25° to 50° C. after release of vacuum. After the paraffinic hydrocarbon liquid has been added, the saturated solution is cooled down to about room temperature or less, e.g. sometimes 0° C., to effectuate precipitation of acrylamide crystals. After the precipitation is complete, the supernatant liquid is removed from the crystalline precipitate and allowed to stand to permit separation of any paraffinic hydrocarbon liquid to occur. This recovered hydrocarbon liquid is available for reuse.

After removal of the liquid from the crystalline mass, the crystalline acrylamide is allowed to drain for a period of time ranging between ½ hour - 5 hours, with 2 hours being adequate in most instances. This drainage of fluid produces two fractions with the upper layer being the paraffinic hydrocarbon liquid and the lower layer being an aqueous solution substantially saturated with acrylamide. The acrylamide rich solution is saved and returned for subsequent reprocessing, whereas the hydrocarbon layer is saved for further use in the process or for reuse.

At this point, the crystalline acrylamide may be further dried by heat and/or vacuum means or may be added to fresh water such as deionized water, to prepare solutions from which polymers can be made or for purposes of storage or shipping.

As mentioned earlier, when the acrylamide is produced by the catalytic hydration of acrylonitrile and water, the acrylamide is oftentimes contaminated with trienamide. When this occurs, it is necessary to further wash the crystals prepared as described above to substantially reduce the trienamide level within acceptable limits. Unless the trienamide is 0.001% by weight or less of the dry acrylamide, its presence interferes with the production of high molecular weight polymers prepared from acrylamide which is contaminated with this impurity.

To remove the trienamide to acceptable levels, the invention contemplates one or more washings of the drained crystals with from about 2 to 10% by weight of water which is a solvent for the trienamide. It has been found that this washing with small amounts of wash water will only be successful in removing trienamide when the crystals are first slurried in the water insoluble paraffinic hydrocarbon liquid. Thus, crystals processed as previously described are re-slurried in sufficient paraffinic hydrocarbon liquid to render the entire mass fluid and workable, and to this is added the amounts of wash water previously described, mixed for a period of time ranging between 10 – 60 minutes and then allowed to stand, whereby the water and the paraffinic hydrocarbon liquid are drained from the crystalline mass. The drain time may vary between as litte as ½ hour up to 5 hours for each wash cycle used. In most instances, at the end of 3 wash cycles, the trienamide content can be reduced from .003% by weight of crystalline acrylamide to as little as 0.0005% by weight. The recovered wash water and paraffinic hydrocarbon are recovered and reprocessed or reused.

To better illustrate my process, reference may be had to the drawing which is self-explanatory. It shows the various process steps generally described and the conditions under which each step is practiced. This figure is presented for purposes of illustrating one of the best modes of my invention. As an aid to further understanding the drawing, the following additional information is presented:

In this process, the feed stock, consisting of 100 parts of deionized monomer solution (48.2 parts acrylamide) is combined with recycled mother liquor and rinse liquor and inhibited with 25 ppm copper ion. After vacuum stripping to increase the acrylamide concentration to 83%, 55.6 parts of Isopar M is added to the hot (50° C) concentrate. By cooling this mixture to 25° C, a three phase Isopar/acrylamide crystal/mother liquor slurry is formed. By opening a valve in the bottom of the crystallizer, 48.7 parts of mother liquor are drained out in 2 hours or less. In addition, 31 parts of Isopar M is also drained out and is decanted from the mother liquor and returned to the crystals to keep the mixture fluid.

The stirred mass of acrylamide crystals in Isopar M is rinsed by adding 4.6 parts of water. The resulting mixture is allowed to settle and drain for 5 hours. Approximately 36 parts of Isopar M in the drainage fluid is decanted and returned to the crystals. The mixture is stirred again and once more 4.6 parts of water are added to rinse the crystals. Then the mixture is again allowed to settle and drain for 5 hours. Approximately 37.5 parts of Isopar M in the drainage fluid is decanted and saved for the next cycle. Combined aqueous phases from the rinse drains averaged 25.3 parts with 60 to 70% of the total recovered during the second rinse draining operation. At this point, 46.3 parts of water are added to dissolve the remaining acrylamide crystals in the Isopar slurry and heat is supplied to bring the temperature to 25° C. After draining the two (liquid) phase mixture from the crystallizer, approximately 17 parts of Isopar M are decanted and saved for the next run. Approximately 94 parts of purified crystal solution (45.5 parts acrylamide) are produced per cycle (FIG. 1). Overall yield of acrylamide after 7 cycles was 86% of the feed acrylamide.

This crystal solution monomer was found to be suitable for the production of medium to high activity acrylamide polymer.

Having thus described my invention, it is claimed as follows:

1. A method of improving mother liquor removal from acrylamide crystals which comprises the steps of precipitating the acrylamide crystals from their mother liquor in the presence of a water-insoluble paraffinic hydrocarbon liquid and allowing the mother liquor entrained within said crystals and the water-insoluble paraffinic hydrocarbon liquid to drain therefrom and then recovering the acrylamide crystals.

2. The process of claim 1 where the drained crystals are treated at least once by slurrying them in additional water-insoluble paraffinic hydrocarbon liquid and washing them with water and then separating the crystals from the wash water and water-insoluble paraffinic hydrocarbon liquid.

3. The method of claim 2 where the wash water and water-insoluble paraffinic hydrocarbon liquid are recovered, separated and the water-insoluble paraffinic hydrocarbon liquid is reused.

* * * * *